United States Patent [19]

Komori et al.

[11] Patent Number: 5,211,941
[45] Date of Patent: May 18, 1993

[54] HAIR CLEANSING COMPOSITION

[75] Inventors: Takashi Komori, Sakura; Yoshiyuki Eshita, Chiba; Tsuyoshi Ohtomo, Miyashiromachi; Hajime Hirota, Tokyo, all of Japan

[73] Assignee: Kao Corporation, Tokyo, Japan

[21] Appl. No.: 712,416

[22] Filed: Jun. 10, 1991

[30] Foreign Application Priority Data

Jun. 11, 1990 [JP] Japan .................. 2-152191
Jun. 11, 1990 [JP] Japan .................. 2-152192

[51] Int. Cl.$^5$ ............................. A61K 7/075
[52] U.S. Cl. ........................ 424/70; 424/71
[58] Field of Search ............ 424/70, 71; 514/784, 514/785, 881, 788, 76, 77; 252/DIG. 13

[56] References Cited

U.S. PATENT DOCUMENTS

| | | | |
|---|---|---|---|
| 4,139,485 | 2/1979 | Imokawa et al. | 252/DIG. 13 |
| 4,536,519 | 8/1985 | Suzuki et al. | 514/847 |
| 4,758,376 | 7/1988 | Hirota et al. | 424/70 |
| 4,868,163 | 9/1989 | Takei et al. | 514/784 |
| 5,015,471 | 5/1991 | Birtwistle et al. | 424/70 |

FOREIGN PATENT DOCUMENTS

| | | |
|---|---|---|
| 0227012 | 7/1987 | European Pat. Off. . |
| 0265702 | 5/1988 | European Pat. Off. . |
| 1098828 | 8/1955 | France . |
| 2618351 | 7/1987 | France . |

OTHER PUBLICATIONS

Chemical Abstracts, vol. 85, No. 14, 1976, No. 99026c.

Primary Examiner—Thurman K. Page
Assistant Examiner—D. Colucci
Attorney, Agent, or Firm—Oblon, Spivak, McClelland, Maier & Neustadt

[57] ABSTRACT

There is disclosed a hair cleansing composition having excellent detergency against oily dirts such as aged high-viscosity silicone compounds. The composition comprises the following components (a) to (d):

(a): 0.05 to 15% by weight of a surfactant,
(b): 0.5 to 40% by weight of an alcohol,
(c): 0.1 to 25% by weight of water, and
(d): 20 to 98% by weight of a liquid oil, wherein a viscosity ratio of a mixture of the components (a) to (c) to a mixture of oil components comprising component (d) is 1 or more.

5 Claims, No Drawings

HAIR CLEANSING COMPOSITION

BACKGROUND OF THE INVENTION

1. Field of the Invention

The present invention relates to a hair cleansing composition and more specifically to a hair cleansing composition containing a large quantity of a liquid oil, and has an excellent detergency against polymers such as a high-viscosity silicone compound contained in hair-care products, against scum and sparingly soluble, aged sebum dirts, and provides good feeling upon use.

2. Description of the Background Art:

Hair cleansers are used to remove dirts from the scalp and hair fibers to keep them clean and to normalize the physiological action thereof to maintain the health of the scalp as well as to make the hair fibers beautiful. They contain, as primary active ingredients, anionic, amphoteric and/or nonionic surfactants. Recently, in order to reduce friction and irritation which may be encountered in shampooing and to avoid excessive defatting caused by an increased frequency of shampooing, low-irritative detergent surfactants and various kinds of conditioners such as polymers have come to be incorporated into hair cleansing compositions.

Meanwhile, high-viscosity silicones and anti-moisture setting polymers are usually incorporated into hair-care products to improve their functions. However, they are difficult to be removed by conventional shampoos.

Insufficient removal of these polymers and sebaceous matters from the scalp and hair fibers is liable to cause various troubles such as lost of hair gloss, the split hair, dry and rough hair fibers, lack of smoothness, less elasticity, difficult hair styling and trangling of the hair.

Accordingly, there has been desired hair cleansing compositions which are mild to the scalp and hair fibers and can readily remove high-viscosity silicones and sebum dirts which are difficult to be removed by conventional shampoos.

Under such circumstances, extensive studies made by the present inventors have resulted in finding that a hair cleansing composition comprising aqueous components which are a surfactant, an alcohol and water and oil components which include a liquid oil having a lower viscosity than that of the aqueous components is mild to the scalp and hair fibers and can readily remove high-viscosity silicones and sebum dirts which are difficult to be removed by conventional shampoos and that it provides good feeling upon use and has excellent stability. Further, the inventors have found that a hair cleansing composition comprising a branched monoalkyl phosphate and another surfactant in combination as a surfactant; alcohol; water; and silicone oil as a liquid oil can easily remove high-viscosity silicone compounds and is mild to the scalp and hair fibers.

SUMMARY OF THE INVENTION

An object of this invention is to provide a hair cleansing composition containing the following components (a) to (d):

(a): 0.05 to 15% by weight of a surfactant,
(b): 0.5 to 40% by weight of an alcohol,
(c): 0.1 to 25% by weight of water, and
(d): 20 to 98% by weight of a liquid oil, a viscosity ratio of a mixture consisting of said components (a), (b) and (c) to a mixture of oil components comprising component (d) being 1 or more.

DETAILED DESCRIPTION OF THE INVENTION AND PREFERRED EMBODIMENTS

In this specification, the term "hair cleanser" or "hair cleansing composition" broadly encompasses not only ordinary shampoos in a classical sense, but also pre-shampoos, hair-make removers, dandruff removers, hair conditioners and the like.

Furthermore, the term "oil component" means not only the liquid oil defined as component (d) but also any other cosmetically acceptable oils and fats and oil-soluble polymers which are optionally and generally adopted in this technical field. A mixture of the oil components desirably has a viscosity of 100 cs or less at 25° C.

Examples of the surfactant of component (a) are nonionic surfactants such as monoglycerides, sorbitan fatty acid esters, sucrose fatty acid esters, polyglycerol fatty acid esters, alkanol amides, amine oxides, polyoxyethylene alkyl ethers, polyethylene glycol fatty acid esters, polyoxyethylene sorbitan fatty acid esters, Pluronic, polyoxyethylene glycerol fatty acid monoesters, polyoxyethylene propylene glycol fatty acid monoesters, polyoxyethylene hydrogenated caster oils, polyoxyethylene fatty acid amides, polyoxyethylene alkylamines and alkyl saccharides; anionic surfactants such as alkyl sulfates, alkyl ether sulfates, fatty acid soaps, ether carboxylic acids and salts thereof, alkane sulfonic acid salts, $\alpha$-olefin sulfonic acid salts, sulfonic acid salts of higher fatty acid esters, dialkyl sulfosuccinates, monoalkyl sulfosuccinates, polyoxyethylene monoalkyl sulfosuccinate, sulfonic acid salts of higher fatty acid amides, sulfuric acid ester salts of glycerol fatty acid esters, sulfuric acid ester salts of higher fatty acid alkylolamides, acylated amino acid salt and monoalkyl phosphates; cationic surfactants such as alkyl trimethyl ammonium salts, dialkyl dimethyl ammonium salts, alkyl dimethyl benzyl ammonium salts, alkyl pyridinium salts and alkyl isoquinolinium salts; and amphoteric surfactants such as imidazoline type, amido amino acid salts, alkyl betain type, and alkyl sulfobetain type. These surfactants of component (a) are used solely or in combination and incorporated by 0.05 to 15% by weight (hereinafter referred to as %), preferably 0.1 to 5% based on the total composition.

Examples of the alcohols of component (b) are monoalcohols such as ethanol; and polyols such as glycerol, ethylene glycol, diethylene glycol, triethylene glycol, hexanediol, butylene glycol, heptanediol, propylene glycol, sorbitol, maltitol, and polyethylene glycol. Of them, especially preferred are ethanol, glycerol, propylene glycol, butylene glycol, sorbitol, and polyethylene glycol.

These alcohols are used solely or in combination, and incorporated by 0.5 to 40%, preferably 2 to 30% based on the total composition.

The water which is component (c) is incorporated by 0.1 to 25%, more preferably 1 to 15%, based on the total composition.

The liquid oil of component (d) is not limited as far as it is liquid at 25° C. Examples thereof are 4 and 5-membered volatile cyclic silicone compounds, dimethyl polysiloxane of 100 cs or less, methyl phenyl polysiloxane of 100 cs or less, squalane, hydrocarbons such as liquid paraffin and isoparaffin, branched fatty acid, higher fatty acid esters, benzoates, triglycerides, diglycerides, and rosin derivatives. Of them, more preferred are cyclic silicone compounds, dimethyl polysiloxane and methyl phenyl polysiloxane of 20 cs or less, isoparaffin of 20 cs or less, fatty acid alcohol ester, diglycerides and triglycerides. Here, "liquid at 25° C." in this invention is determined as follows: In a flat-bottom test tube (inner diameter: 30 mm, height: 120 mm) having bench marks at the heights of 55 mm (A) and 85 mm (B) from the bottom, a sample is placed to the level of mark A. The test tube is bathed in 25° C. water for more than 10 minutes and then, it is laid down on a horizontal plate. Samples which reach mark B within 90 seconds are taken as "liquid at 25° C.".

These oils are used solely or in combination, and incorporated by 20 to 98%, preferably 50 to 98% based on the total composition.

In this invention, oil components containing component (d) are kept stable as an O/W emulsion. It is necessary that the viscosity ratio of a mixture of aqueous components (a) to (c) to a mixture of oil components containing component (d) is 1 or more. The ratio less than 1 unfavorably makes it impossible to stably incorporate a large amount of the oil components, which causes floating and separating of oils, and furthermore, undesirable appearance and insufficient performance. In hair cleansing composition of the invention comprising the above components (a) to (d), excellent detergency against dirts and mildness to the scalp and hair fibers are obtained without controlling the viscosity ratio of the aqueous component mixture of (a) to (c) to the oil component mixture containing component (d) if a specifically branched monoalkyl phosphate and a surfactant having no phosphoric residue and having a specified solubility are used in combination. More specifically, this hair cleansing composition contains the following components (a-1), (a-2), (b), (c) and (d-1) (hereinafter referred to as a MAP-containing hair cleanser):

(a-1): Salt of monoalkyl phosphate represented by the following formula (I):

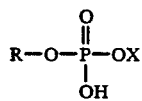

wherein R represents a β-branched alkyl group having 8 to 36 carbon atoms, and X represents an alkali metal, basic amino acid or an organic base;

(a-2): Surfactant having no phosphoric residue and having solubility of 1% by weight or more in 25° C. purified water;

(b): Alcohol;

(c): Water; and (d-1): Silicone oil.

Compounds (I) usable as the above component (a-1) have a branch at the β-position of the alkyl group. They can be prepared by such methods as disclosed in Japanese Patent Application Laid-Open to the Public (Kokai) 58-180496 and 61-17594. Among the compounds (I), more preferable ones are those of formula (II) having a β-branched alkyl group:

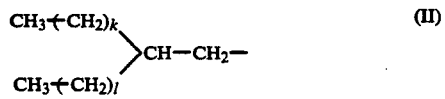

wherein k represents an integer of 2 to 18; l represents an integer of 2 to 14, provided that k+l makes 4 to 32, preferably 10 to 18; counter ion X is an alkali metal such as lithium, potassium and sodium, basic amino acid such as arginine, ornithine, lysin and oxylysin, or alkanol amines having a hydroxyalkyl group of 2 to 3 carbon atoms such as triethanol amine and monoethanol amine.

Component (a-2) which is a surfactant having no phosphoric residue and a solubility of 1% by weight or more in purified water encompasses all of the surfactants defined for component (a) except monoalkyl phosphates. Preferable ones are those having a high hydrophlicity. Examples of the silicone oil used as component (d-1) are 4 or 5-membered volatile, cyclic silicone compounds, dimethyl polysiloxanes having a viscosity of 1 to 1000 cs, and methyl phenyl polysiloxanes having a viscosity of 1000 cs or less, preferably 4 or 5-membered dimethyl polysiloxanes, dimethyl polysiloxanes having a viscosity of 100 cs or less, and methyl phenyl polysiloxanes having a viscosity of 100 cs or less.

Preferable proportion of components (a-1) to (d-1) in the MAP-containing hair cleansing composition are 0.05 to 5%, particularly 0.1 to 2% for (a-1); 0.1 to 25%, particularly 0.5 to 5% for (a-2); 0.5 to 40%, particularly 2 to 30% for (b); 0.5 to 50%, particularly 2 to 30% for (c); and 10 to 98%, particularly 50 to 98% for 2 to 30% for (c); and 10 to 98%, particularly 50 to 98% for (d-1). If the proportions of components (a-1), (b) and (c) fall outside the above preferable ranges, lamella liquid crystal or liposome structures cannot be formed, which makes it difficult to hold a large amount of silicone oil of component (d-1) stably.

The component (d-1) less than 10% cannot sufficiently liberate dirts of hair cosmetic products while the same exceeding 98% unfavorably results in relatively reduced contents of the other components. The component (a-2) less than 0.1% cannot sufficiently remove dirts by a lot of water together with the component (d-1) while the same exceeding 25% unfavorably irritates the scalp and hair fibers.

The MAP-containing hair cleansing composition may further contain a non-siloxane type oil component. This oil component is exemplified by the non-siloxane type oil components which are defined for the component (d) and are liquid at 25° C. Especially preferred are glycerol diesters of one or two fatty acids such as squalane, 2-ethyl cyclohexane acid, myristic acid, oleic acid, and isostearic acid; glycerol triester of one or two fatty acids such as 2-ethyl cyclohexane acid, myristic acid, oleic acid, and isostearic acid; octyldodecyl myristate; and isopropyl myristate. These oil components have an action of liberating dirts cooperatively with component (d-1). The proportion of the oil components is 50% or less based on the total composition.

In addition to the requisite components mentioned above, the hair cleansing composition of the invention including the MAP-containing hair cleanser can further contain conventional components such as a moisturizing agent, a blood circulation promoting agent, a cooling agent, a UV absorber or reflector, an anti-sweating agent, a fungicide, a skin activator, an anti-senescence agent, a perfume, and a colorant.

The hair cleansing composition of the invention can be prepared by conventional methods. Especially preferable preparation method is that first the aqueous components (a) to (c) are mixed and agitated to make them a uniform solution and then the solution is stirred while adding slowly oil components. This process is usually carried out at room temperature but may be done while heating the components if they are solid at room temperature.

The hair cleansing composition of the invention is a transparent or translucent uniform gel having a viscosity of 10,000 cs or more at 25° C. It may optionally be added with pigments and/or colorants. It has such applications as a shampoo, a preshampoo, a hair-make remover, a dandruff remover or the like.

The hair cleansing composition of the invention contains a large amount of liquid oil as an O/W emulsion and is a transparent or translucent gel. It is applied onto the scalp or hair fibers, and subsequent massage can help the oil components quickly spread on the scalp and hair fibers. The spread oil components dissolve or liberate oily dirts accumulated on the scalp and hair fibers. Then, a lot of water applied for rinsing helps the oil components containing the dirts self-emulsify to wash them down. Accordingly, high-viscosity silicone compounds and setting polymers which are difficult to be removed by conventional shampoos can readily be removed. Also, it is mild to the scalp and to hair fibers and has a good feeling upon use.

Further, the hair cleansing composition of this invention has another application as a conditioner because of a lot of liquid oil contained therein. It can also readily supply oil-soluble ingredients to the scalp and hair fibers, which have so far been deemed as being difficult to be supplied. Particularly, the MAP-containing hair cleansing composition containing a salt (I) of monoalkyl phosphate is characteristic in that the salt (I) forms a lamella liquid crystal structure or a liposome (vesicle) structure together with water and alcohols even at a low concentration, and it is considered that the oil components such as silicone oil are retained stably in those structures to form a transparent or translucent, uniform MAP-containing hair cleansing composition. Consequently, it can provide an especially excellent property to wash out oily dirts on the hair fibers.

EXAMPLES

The present invention will further be explained with reference to the examples, which however should not be construed as limiting the invention thereto.

EXAMPLE 1

Hair Cleanser

Hair cleansing compositions as shown in Table 1 were prepared and subjected to a sensual test by female panelers. The results are shown in Table 2.

TABLE 1

| Component (%) | Invention Product 1 | Comparison Product A | Comparison Product B |
|---|---|---|---|
| 1) Polyoxyethylene (20) hydrogenated castor oil | 2.0 | 2.0 | 2.0 |
| 2) Glycerol | 5.0 | 5.0 | 5.0 |
| 3) Water | 3.0 | 3.0 | 3.0 |
| 4) 4-Membered dimethyl polysiloxane (SH244 manufactured by Toray Silicone Co.) | 80.0 | — | — |
| 5) Liquid paraffin (Hicol K-350 by Kaneda Co., Ltd.) | — | 90.0 | — |
| 6) Dimethyl polysiloxane (200 cs) | 10.0 | — | 90.0 |
| Viscosity ratio (aqueous components/ | 2.5 | 0.35 | 0.25 |

TABLE 1-continued

| Component (%) | Invention Product 1 | Comparison Product A | Comparison Product B |
|---|---|---|---|
| oil components) | | | |

Preparation

The components 1) to 3) were mixed to dissolve. (If necessary, heat may apply.) Then, the oil components were slowly added thereto while stirring.

Evaluation

The compositions thus prepared were sensually evaluated in terms of detergency, feeling upon cleansing and rinsing, touch of the hair when dried, touch of the hair in the next morning, and overall evaluation by twenty female panelers who usually used various styling compositions containing one or more kinds of anionic, amphoteric and nonionic polymers of 0.01 to 10% and high-viscosity dimethyl polysiloxane of 0.01 to 10%. The results are shown in Table 2. The evaluation criteria are classified as follows:

1. Detergency
   ⊚: Feeling of perfect detergency
   ○: Feeling of good detergency
   Δ: Feeling of slightly insufficient detergency
   ×: Feeling of insufficient detergency and sticky
2. Feeling upon cleansing and rinsing
   ⊚: Good finger-passing through hair fibers without catching
   ○: Good finger-passing with little catching
   Δ: Slightly inferior finger-passing with a little catching
   ×: Inferior finger-passing with catching
3. Touch to the hair when dried and in the next morning
   ⊚: Smooth and excellent
   ○: Fairly smooth
   Δ: A little sticky
   ×: Sticky and disagreeable
4. Overall rating
   ⊚: Excellent
   ○: Fairly good
   Δ: A little poor
   ×: Poor

TABLE 2

| | Invention Product 1 | Comparison Product A | Comparison Product B |
|---|---|---|---|
| Detergency | ⊚ | Δ | × |
| Feeling upon Cleansing | ⊚ | × | Δ |
| Feeling upon Rinsing | ⊚ | × | Δ |
| Touch to the hair when dried | ⊚ | Δ | Δ |
| Touch in the next morning | ⊚ | Δ | Δ |
| Over all evaluation | ⊚ | Δ | × |

As apparent from Table 2, the Invention product 1 had excellent detergency and good feeling upon use, while Comparisons A and B had inferior appearance and stability, poor detergency and feeling upon use.

EXAMPLE 2

Hair-make Remover

The hair-make removers having the following comositions were prepared and evaluated. Comparison products C and D were evaluated for comparison, wherein Comparison C was an aqueous shampoo containing 20% of sodium alkyl ether phosphate and Comparison D was silicone-removing lotion containing liquid paraffin (90%), olive oil (5%) and hydrogenated castor oil (5%).

Composition

| | | |
|---|---|---|
| 1) Polyoxyethylene (3) lauryl sulfosuccinate.2Na | 3.0% | |
| 2) Glycerol | 7.0 | |
| 3) Water | 5.0 | |
| 4) Oil[note] | 85.0 | |

[note] Invention Product 2: 4-membered dimethyl polysiloxane (SH244 produced by Toray Silicone)
Invention 3: Dimethyl polysiloxane (2 cs)

Preparation

The components 1) to 3) were agitated to form a uniform solution at room temperature and then, component 4) was slowly added thereto, followed by stirring for further 30 minutes. The viscosity ratios of a mixture of the aqueous components to a mixture of the oil components were 20 in Invention Product 2 and 15 in Invention Product 3, respectively.

Evaluation

Dimethyl polysiloxane having an average molecular weight of 100,000 was applied as dirts to 20 cm hair fibers sampled from a Japanese woman to prepare hair samples for test. Each hair sample was cleansed with each of the test compositions (0.5 g of test composition per 10 g of hair sample). Then, it was dried and subjected to extraction of the residual polymer with chloroform to measure the Si amount by means of atomic luminescence analysis. The measured values converted to the amounts of dimethyl polysiloxane are shown in Table 3.

TABLE 3

| | Invention Product 2 | Invention Product 3 | Comparison Product C | Comparison Product D |
|---|---|---|---|---|
| Residual Amount μg/g hair | 50 or less | 50 or less | 700 | 800 |

Note: Initial amount of dimethyl polysiloxane coating: 950 μg/g hair

EXAMPLE 3

Point-set Remover

Point-set removers as shown in Table 4 were prepared and evaluated.

TABLE 4

| Components (%) | Invention Product 4 | Invention Product 5 |
|---|---|---|
| 1) Cocoyl methyl taurine sodium salt | 1.5 | 1.5 |
| 2) Polyoxyethylene (3) laurylether sulfate.Na (25%) | 4.5 | 4.5 |
| 3) 1,3-Butylene glycol | 5.0 | 5.0 |
| 4) Polyethyleneglycol 1500 | 1.0 | 1.0 |
| 5) Water | 3.0 | 3.0 |
| 6) 5-Membered dimethyl polysiloxane (SH245 produced by Toray Silicone | 85.0 | — |
| 7) Isopropyl palmitate | — | 50.0 |
| 8) 2-Ethyl hexanoic triglyceride | — | 35.0 |
| Viscosity ratio (aqueous components/oil components) | 20 | 2.5 |

Preparation

The components 1) to 5) were mixed and dissolved. Then, the components 6) or 7) and 8) were slowly added thereto while stirring, followed by stirring for further 30 minutes.

Evaluation

The composition samples were tested by ten female panelers who used abundant style keeping compositions containing a polymer Gantrez ES-425 (manufactured by GAF Chemicals Co.) to evaluate easiness of removing the styling composition, easiness of finger-passing through hair fibers when hair-cleansing, lightness, softness, and lubricantness after dried. The results are shown in Table 5. The evaluation criteria are as follows:

⊙: Rated as good by 8 or more of ten panelers
○: Rated as good by 6 to 7 of ten panelers
△: Rated as good by 4 to 5 of ten panelers
×: Rated as good by 3 or by less of ten panelers

TABLE 5

| Evaluation Items | Invention Product 4 | Invention Product 5 |
|---|---|---|
| Easiness of removing a styling composition | ⊙ | ⊙ |
| Easiness of finger-passing through hair fibers in cleansing | ⊙ | ⊙ |
| Lightness after dried | ⊙ | ○ |
| Moistness after dried | ○ | ⊙ |
| Lubricantness after dried | ⊙ | ○ |

The compositions 4 and 5 of the invention had good detergency and favorable feeling upon use.

EXAMPLE 4

Dandruff Remover

A dandruff remover of the following formulation was prepared, wherein the viscosity ratio of a mixture of the aqueous components to a mixture of oil components was 1.5.

The remover was rubbed well on the scalp, and when rinsed away after a while, the dandruffs sticked on the scalp were removed without irritation.

Composition

| | |
|---|---|
| 1) Polyoxyethylene (80) hydrogenated castor oil | 1.5% |
| 2) Glycerol | 10.0 |
| 3) 1,3-Butylene glycol | 5.5 |
| 4) Water | 10.0 |
| 5) Olive oil | 20.0 |
| 6) 2-Ethyl hexanoic diglyceride | 40.0 |
| 7) Polyisobutene | 13.0 |

EXAMPLE 5

Preshampoo

A preshampoo having the following formulation was prepared, wherein the viscosity ratio of the aqueous components to the oil components was 10.

This preshampoo enabled to shampoo even long or waved hair with no tangling while passing fingers through hair fibers.

Composition

| | |
|---|---|
| 1) Lauroyl methyl taurine.Na | 1.0% |
| 2) Polyoxyethylene (3) lauryl sulfosuccinate.2Na | 1.0 |
| 3) Glycerol | 5.0 |
| 4) Water | 8.0 |
| 5) 4-Membered dimethyl polysiloxane | 50.0 |

-continued

| | |
|---|---|
| 6) 5-Membered dimethyl polysiloxane | 35.0 |

EXAMPLE 6

Shampoo for Oily Dirts

A shampoo for oily dirts having the following composition was prepared.

Composition

| | |
|---|---|
| 1) Polyoxyethylene (3) lauryl sulfosuccinate.2Na | 10.0% |
| 2) Glycerol | 10.0 |
| 3) Water | 2.0 |
| 4) Dimethyl polysiloxane (2 cs) | 55.0 |

Preparation

The component 4) was added to the composition consisting of components 1) to 3) at room temperature to prepare a shampoo for oily dirts, wherein the viscosity ratio of a mixture of the aqueous components to a mixture of the oil components was 10.

This shampoo enabled to remove the oily dirts on the scalp and hair fibers and to provide refreshness and moistness.

EXAMPLE 7

Shampoo

Jelly shampoos of the compositions shown in Table 6 were prepared in the following manner and subjected to the sensual evaluation in the same manner as in Example 1. The results are shown in Table 7.

TABLE 6

| Components (%) | Invention Product 6 | Comparison Product E | Comparison Product F |
|---|---|---|---|
| 1) 2-Octalauryl phosphate arginine salt | 0.5 | 0.5 | 0.5 |
| 2) Sodium oleate | 1.0 | — | 1.0 |
| 3) Polyoxyethylene sorbitan (20 E.O.) stearyl ester | 1.0 | — | 1.0 |
| 4) Glycerol | 3.0 | 3.0 | 3.0 |
| 5) Water | 8.0 | 8.0 | 8.0 |
| 6) Dimethyl polysiloxane (2 cs) | 50.0 | 50.0 | — |
| 7) Liquid paraffin (Hicol K-350 by Kaneda) | 36.5 | 38.5 | 86.5 |

Preparation

The components 1) to 5) were dissolved and stirred at 60° C. for one hour. Then, after cooled to room temperature, the components 6) and 7) were slowly added thereto while stirring.

TABLE 7

| Evaluation Items | Invention Product 6 | Comparison Product E | Comparison Product F |
|---|---|---|---|
| Detergency | ⊙ | Δ | X |
| Feeling upon shampooing | ⊙ | X | X |
| Feeling upon rinsing | ⊙ | X | Δ |
| Touch to the hair when dried | ⊙ | Δ | Δ |
| Touch in the next morning | ⊙ | Δ | Δ |

TABLE 7-continued

| Evaluation Items | Invention Product 6 | Comparison Product E | Comparison Product F |
|---|---|---|---|
| Overall evaluation | ⊙ | Δ | X |

EXAMPLE 8

Hair-make Remover

Hair-make removers having the following formulations were prepared in the following manner and subjected to the measurement of a residual amount of dirts on the hair fibers in the same manner as in Example 2 to evaluate detergency. The results are shown in Table 8. Comparison Products G and H were also evaluated for comparison, wherein Comparison G is an aqueous shampoo containing 20% sodium alkyl phosphate, and Comparison H is a silicone-removing lotion containing liquid paraffin (90%), olive oil (5%) and hydrogenated castor oil (5%).

Composition

| | |
|---|---|
| 1) 2-Hexyldecyl phosphate arginine salt | 0.3% |
| 2) Glycerol | 4.0 |
| 3) Water | 5.0 |
| 4) POE(3) lauryl ether sulfate.Na (25%) | 2.5 |
| 5) POE(20) sorbitan monopalmitate | 0.5 |
| 6) Oils[note] | 87.7 |

[note]Invention Product 7: 4-Membered dimethyl polysiloxane (SH244 made by Toray silicone) 50.0% Dimethyl polysiloxane (100 cs) 37.7
Invention Product 8: 5-Membered dimethyl polysiloxane (SH245 made by Toray silicone) 70.0 Liquid Paraffin 17.7

Preparation

The components 1) to 5) were stirred to a uniform solution at room temperature and then, the component 6) was added thereto.

TABLE 8

| | Invention Product 7 | Invention Product 8 | Comparison Product G | Comparison Product H |
|---|---|---|---|---|
| Residual amount μg/g of hair | 50 or less | 100 | 700 | 900 |

Note: Initial amount of dimethyl polysiloxane coating: 1000 μg/g of hair

EXAMPLE 9

Point-set Remover

Point-set removers are shown in Table 9 were prepared in the following manner and subjected to the following sensual evaluation. The results are shown in Table 10.

TABLE 9

| | Invention Product 9 | Comparison Product I |
|---|---|---|
| 1) 2-Hexyldecyl phosphate arginine salt | 1.0 | — |
| 2) Water | 8.0 | 8.0 |
| 3) Glycerol | 3.0 | 3.0 |
| 4) Propylene glycol | 3.0 | 3.0 |
| 5) POE(50) hydrogenated castor oil | 2.0 | 2.0 |
| 6) Lauroyl sodium sarcosinate | 3.0 | 3.0 |
| 7) Methyl phenyl polysiloxane (10 cs) | 50.0 | 50.0 |
| 8) Liquid paraffin | 30.0 | 31.0 |

TABLE 9-continued

|  | Invention Product 9 | Comparison Product I |
|---|---|---|
| (Hicol K-350) |  |  |

Preparation

The components 1) to 6) were mixed and dissolved, and then the components 7) and 8) were added slowly while stirring.

Evaluation

The point-set removers thus prepared were used by ten female panelers who used abundant style keeping compositions (Gantrez ES225 manufactured by GAF Chemicals Co.) to evaluate the items shown in Table 10. The results are classified based on the following criteria:

⊚: Rated as good by 8 or more of ten panelers
○: Rated as good by 6 to 7 of ten panelers
△: Rated as good by 4 to 5 of ten panelers
×: Rated as good by 3 or less of ten panelers

TABLE 10

| Evaluation Items | Invention Product 9 | Comparison Product I |
|---|---|---|
| Easiness of removing a styling composition | ⊚ | △ |
| Easiness of finger-passing through hair fibers in cleansing | ⊚ | ○ |
| Easiness upon use | ⊚ | × |
| Lightness after dried | ⊚ | × |
| Lubricantness after dried | ○ | × |

EXAMPLE 10

Dandruff Remover

A dandruff remover having the following composition was prepared. It was rubbed well onto the scalp and when rinsed away after a while, the dandruffs sticked on the scalp were removed without irritation.

Composition

| 1) 2-Octyldodecyl phosphate arginine salt | 0.6% |
|---|---|
| 2) Water | 7.4 |
| 3) 1,3-Butylene glycol | 10.0 |
| 4) Sodium alkyl sulfate (C = 12) | 2.0 |
| 5) Olive oil | 40.0 |
| 6) Methyl phenyl polysiloxane (50 cs) | 40.0 |

EXAMPLE 11

Preshampoo

Preshampoos having the following formulations were prepared. These preshampoos enabled to shampoo even long or waved hair with no tangling while passing fingers through hair fibers and to remove dirts easily.

Composition a

| 1) 2-Hexyldecyl phosphate arginine salt | 0.5% |
|---|---|
| 2) Water | 50.0 |
| 3) Glycerol | 26.5 |
| 4) Sodium lauroyl methyl taurine | 3.0 |
| 5) Dimethyl polysiloxane (10 cs) | 15.0 |
| 6) Dimethyl polysiloxane (50 cs) | 5.0 |

Composition b

| 1) 2-Heptylundecyl phosphate arginine salt | 1.0 |
|---|---|
| 2) Water | 46.0 |
| 3) Ethanol | 5.0 |
| 4) Glycerol | 30.0 |
| 5) Polyoxyethylne (20 E.O.) sorbitan oleyl ester | 3.5 |
| 6) 4-Membered dimethyl polysiloxane (SH244) | 10.0 |
| 7) Olive oil | 5.0 |
| 8) Stearyl trimethyl ammonium chloride | 0.5 |

EXAMPLE 12

Shampoo for oily dirts

The following components 5) to 7) were added slowly to the aqueous composition consisting of the components 1) to 4) at room temperature to prepare a shampoo for oily dirts.

Composition

| 1) 2-Hexyldecyl phosphate arginine salt | 0.5% |
|---|---|
| 2) Disodium POE (3) lauryl sulfosuccinate | 2.0 |
| 3) Glycerol | 7.5 |
| 4) Water | 10.0 |
| 5) Jojoba oil | 20.0 |
| 6) 4-Membered dimethyl polysiloxane (SH244) | 40.0 |
| 7) 2-Ethyl hexanoic triglyceride | 20.0 |

This shampoo enabled to remove oily dirts on the scalp and hair fibers to provide refreshing and moistened feeling.

What is claimed is:

1. A hair cleansing composition comprising:
   (a) 0.05 to 15% by weight of a surfactant, selected from the group consisting of (1) nonionic surfactants selected from the group consisting of monoglycerides, sorbitan fatty acid esters, sucrose fatty acid esters, polyglycerol fatty acid esters, alkanol amides, amine oxides, polyoxyethylene alkyl ethers, polyethylene glycol fatty acid esters, polyoxyethylene sorbitan fatty acid esters, polyoxyalkylene derivatives of propylene glycol, polyoxyethylene glycerol fatty acid monoesters, polyoxyethylene propylene glycol fatty acid monoesters, polyoxyethylene hydrogenated caster oils, polyoxyethylene fatty acid amides, polyoxyethylene alkylamines and alkyl saccharides; (2) anionic surfactants selected from the group consisting of alkyl sulfates, alkyl ether sulfates, fatty acid soaps, ether carboxylic acids and salts thereof, alkane sulfonic acid salts, α-olefin sulfonic acid salts, sulfonic acid salts of higher fatty acid esters, dialkyl sulfosuccinates, monoalkyl sulfosuccinates, polyoxyethylene monoalkyl sulfosuccinates, sulfonic acid salts of higher fatty acid amides, sulfuric acid ester salts of glycerol fatty acid esters, sulfuric acid ester salts of higher fatty acid alkylolamides, acylated amino acid salts and monoalkyl phosphates; (3) cationic surfactants selected from the group consisting of alkyl trimethyl ammonium salts, dialkyl dimethyl ammonium salts, alkyl dimethyl benzyl ammonium salts, alkyl pyridinium salts and alkyl isoquinolinium salts; and (4) amphoteric surfactants selected from the group consisting of imidazolines, amido amino acid salts, alkyl betains, and alkyl sulfobetains;
   (b) 0.5 to 40% by weight of an alcohol, which is one or more members selected from the group consisting of ethanol, glycerol, ethylene glycol, diethylene glycol, triethylene glycol, hexanediol, butylene glycol, heptanediol, propylene glycol, sorbitol, maltitol and polyethylene glycol;
(c) 0.1 to 25% by weight of water; and
(d) 20 to 98% by weight of a liquid oil, which is one or more members selected from the group consisting of volatile cyclic silicone compounds, dimethyl polysiloxanes having a viscosity of 100 cs or less, methyl phenyl polysiloxane having a viscosity of 100 cs or less, squalane, liquid paraffin, isoparaffin, branched fatty acids, higher fatty acid esters, benzoates, diglycerides, triglycerides, and rosin derivatives; wherein the viscosity ratio of a mixture consisting of said components (a), (b) and (c) to a mixture of oil components comprising component (d) is 1 or more.

2. The composition according to claim 1, which has a viscosity of 10,000 cs or more at 25° C. and is transparent or translucent gel.

3. The composition according to claim 1, which is an O/W emulsion.

4. The composition according to claim 1, wherein the proportion of component (d) is 50 to 98% by weight based on the total composition.

5. A method of removing dirts from hair fibers comprising:
applying the composition of claim 1 directly onto the hair fibers, and
rinsing with water.

* * * * *